Aug. 9, 1955 G. MERRILL Plant Pat. 1,409

PEACH TREE

Filed Oct. 28, 1954

WITNESS

Addison E. Avery

INVENTOR

Grant Merrill

Webster & Webster

ATTYS.

United States Patent Office

Plant Pat. 1,409
Patented Aug. 9, 1955

1,409

PEACH TREE

Grant Merrill, Red Bluff, Calif.

Application October 28, 1954, Serial No. 465,456

1 Claim. (Cl. 47—62)

This invention relates to a new and distinct variety of peach tree which bears commercially desirable fruit quite similar to the clingstone Merrill Gem Peach (United States Plant Patent No. 868), especially as to size and the coloring of the skin and flesh; but advantageously differs therefrom in that here the fruit is a freestone with meaty to melting flesh when soft ripe for dessert and culinary use, although being a clingstone with firm flesh when hard ripe for shipping.

Another distinguishing characteristic of the present variety of peach tree is that the fruit ripens a few days in advance of the Merrill Gem Peach, which is desirable marketwise.

A further characteristic of the present variety of peach tree is that there is a tendency of the fruit to set more heavily than the Merrill Gem Peach, which—while possibly requiring more thinning—assures of substantial average seasonal production.

The parent peach tree of the variety was originated by me, in my experimental orchard located near Red Bluff, California, as a first generation seedling of a cross between the Burbank July Elberta Peach (United States Plant Patent No. 15) and the Merrill Gem Peach (United States Plant Patent No. 868).

Seeds from this cross were planted and among the resulting seedlings, which were carefully observed, one was a very good grower and evidenced desirable characteristics with respect to the fruit, and such seedling—which is the present variety—was therefore selected for propagation.

Subsequent to such selection the variety was asexually reproduced by grafting onto mature Golden Jubilee (unpatented) peach trees in such experimental orchard, and when these grafts came into bearing, they were found to carry forward each and every one of the characteristics of the parent tree.

Figures 1, 2:
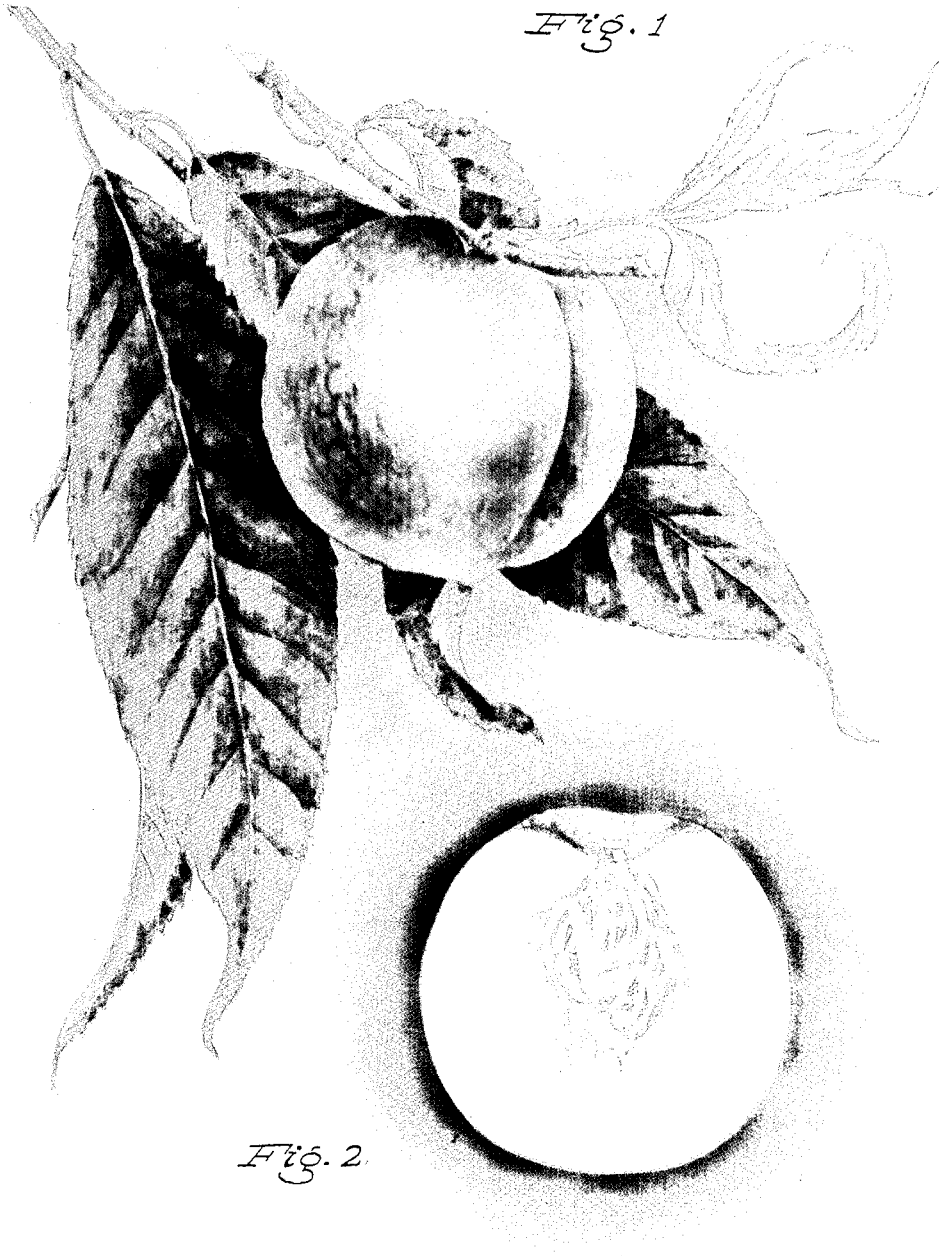
Fig. 1 is a side elevation of one of the fruit, together with twigs and leaves.
Fig. 2 is a sectional elevation of one of the fruit, with the stone exposed.

Referring now more specifically to the pomological details of this new and distinct variety of peach tree, the following is an outline description thereof; all major color plate identifications being by reference to Maerz and Paul Dictionary of Color:

Tree: Medium size; medium vigorous; form and density controlled by pruning; productive; regular bearer.
- *Trunk.*—Medium stocky; medium shaggy.
- *Branches.*—Medium stocky; medium shaggy; reddish brown color.
- *Lenticels.*—Medium quantity; medium size.
- *Leaves.*—Medium size; average length—4" to 7", mostly 5" to 6"; average width—1½" to 1¾"; medium thickness; lanceolate, with tip acuminate; rugose along midrib.
  - Margin—Crenate.
  - Petiole—Medium length; medium slender.

- Glands—None to seven, average two to four; alternate; large; reniform; green; positioned on base of leaves and upper part of petiole.
  - Stipules—On new leaves falling off early.
  - Color—Top side—medium green (22–L–7); under side—lighter green (22–J–5); new leaves—light yellowish green (17–K–4).

Flower buds: Medium size; medium length; plump; free; pubescent.

Flowers: Dates of first and last bloom—March 1, 1954, and March 15, 1954, respectively.
- *Size.*—Medium to small.
- *Color.*—Pink; unopened anthers—orange yellow.
- *Pollen.*—Present.

Fruit:
- *Maturity when described.*—Eating to soft ripe, June 29, 1954, from rank growing young grafts.
- *Date of first picking.*—June 20, 1954, on rank growing young grafts.
- *Date of last picking.*—June 28, 1954, on rank growing young grafts.
- *Size.*—Large; average width, cheek to cheek, 2¼" to 2¾"; average width through suture, 2⅜" to 3"; average length, 2½" to 3".
- *Form.*—Globose, sometimes slightly oblong.
- *Suture.*—A distinct shallow groove extending from base to apex, without depression beyond pistil point. The suture next to the stem end may become a deep groove nearly to the pit on many fruit.
- *Ventral surface.*—Rounded; lips inconspicuous but unequal.
- *Cavity.*—Rounded; abrupt; slightly elongated in suture plane; average depth—⅜" to ½"; average breadth—½" to ¾"; markings—yellow, with red blush dependent on extent of exposure to sunlight.
- *Base.*—Rounded.
- *Apex.*—Short; depressed.
- *Pistil point.*—Apical.
- *Skin.*—Medium thickness; medium tender; free when soft ripe.
- *Tendency to crack.*—None.
  - Color—Yellow under-color, with a deep red blush over a substantial portion of the fruit (3–H–12 shading through 3–L–11), mottled and streaked a deeper red (7–L–6).
- *Flesh.*—
  - Amygdalin—Moderate.
  - Juice—Abundant; rich.
  - Texture—Very firm when hard ripe for shipping; meaty to melty when soft ripe for use.
  - Fibers—Few; fine; tender.
  - Ripens—Evenly.
  - Flavor—Delicate.
  - Aroma—Distinct.
  - Eating quality—Good.
  - Color—Yellow (9–J–2 shading to 9–L–3), mottled with red next to the skin (2–E–11 shading to 3–K–10).
  - Surface of pit cavity—Pale yellow.
- *Stone.*—Cling when hard ripe; nearly free when firm ripe; completely free when soft ripe. Retains short fiber-like threads around the stem end.
  - Size—Medium; average length—1½"; average breadth—1"; average thickness—⅞".
  - Form—Obovate; tip cuspidate.
  - Base—Straight.
  - Hilum—Tends to retain portion of the stem on many fruit; oval.
  - Apex—Cuspidate.

Sides—Usually nearly equal.
Surface—Irregularly furrowed toward apex; pitted toward base.
Ridges—Toward apex; interrupted.
Pits—Elongated.
Ventral edge—Thick with wing toward base.
Dorsal edge—Full with deep narrow grooves throughout, usually larger on one side than on the other.
Tendency to split—None.
Color—Light tan (10–G–5 shading to 10–G–7).

Use:
Market; local; dessert; long distance shipping; culinary.
Keeping quality: Excellent.
Shipping quality: Excellent.

The tree and its fruit herein described may vary in slight detail due to climatic and soil conditions under which the variety may be grown.

Having thus described my invention, I claim:

A new and distinct variety of peach tree, as illustrated and described, which is characterized—in comparison to the clingstone Merrill Gem Peach—by fruit of similar size and coloring of the skin and flesh, but distinguishes therefrom by being a freestone with meaty to melting flesh when soft ripe, and a clingstone with firm flesh when hard ripe; and further characterized by fruit which sets more heavily, and ripens a few days earlier than said Merrill Gem Peach.

No references cited.